United States Patent
Shirahata

(10) Patent No.: US 8,743,118 B2
(45) Date of Patent: Jun. 3, 2014

(54) MEDICAL IMAGE DISPLAY DEVICE AND MEDICAL IMAGE DISPLAY METHOD

(75) Inventor: Takashi Shirahata, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 858 days.

(21) Appl. No.: 12/933,106

(22) PCT Filed: Mar. 13, 2009

(86) PCT No.: PCT/JP2009/054871
§ 371 (c)(1),
(2), (4) Date: Sep. 17, 2010

(87) PCT Pub. No.: WO2009/116465
PCT Pub. Date: Sep. 24, 2009

(65) Prior Publication Data
US 2011/0018871 A1  Jan. 27, 2011

(30) Foreign Application Priority Data
Mar. 21, 2008 (JP) ................. 2008-072807

(51) Int. Cl.
*G06T 15/10* (2011.01)
*G09G 5/00* (2006.01)
*G06K 9/00* (2006.01)
*G06K 9/36* (2006.01)
*G06K 9/22* (2006.01)
*A61B 1/06* (2006.01)
*A63F 9/24* (2006.01)
*G06F 3/048* (2013.01)

(52) U.S. Cl.
USPC ........... 345/427; 345/581; 345/619; 382/128; 382/276; 382/313; 600/160; 600/173; 463/33; 715/850

(58) Field of Classification Search
USPC ........... 345/418–427, 581, 586, 619; 382/128–134, 276, 285, 312, 313; 600/343, 101–183; 463/30–34; 715/848–852
See application file for complete search history.

(56) References Cited

U.S. PATENT DOCUMENTS

| 7,167,180 | B1 | 1/2007 | Shibolet | |
|---|---|---|---|---|
| 2006/0056730 | A1* | 3/2006 | Matsumoto | 382/285 |
| 2006/0238534 | A1 | 10/2006 | Matsumoto | |
| 2006/0252987 | A1* | 11/2006 | Hasegawa et al. | 600/101 |
| 2008/0118117 | A1* | 5/2008 | Gauldie et al. | 382/128 |
| 2008/0175459 | A1* | 7/2008 | Geiger et al. | 382/131 |

FOREIGN PATENT DOCUMENTS

| JP | 7-302110 | 11/1995 |
|---|---|---|
| JP | 2002-504385 | 2/2002 |
| JP | 2006-302103 | 11/2006 |

OTHER PUBLICATIONS

International Search Report in PCT/JP2009/054871.

* cited by examiner

*Primary Examiner* — Wesner Sajous
*Assistant Examiner* — Andrew Shin
(74) *Attorney, Agent, or Firm* — Cooper & Dunham LLP

(57) ABSTRACT

A medical image display device provided with storage means for storing a sliced image of an object to be examined obtained by a medical image diagnostic apparatus, extraction means for extracting a center line passing through the region of a hollow organ of the object and the center thereof from the sliced image stored by the storage means, and 3-dimensional image generation means for generating a virtual 3-dimensional image of the inner wall of the hollow organ seen from a viewpoint while sequentially moving the viewpoint from one end to the other end of the center line is provided, with means for changing the direction in which the virtual 3-dimensional image seen from the viewpoint is generated to the direction of bending curvature of the hollow organ according to the bending curvature thereof.

4 Claims, 12 Drawing Sheets

Figure 1:
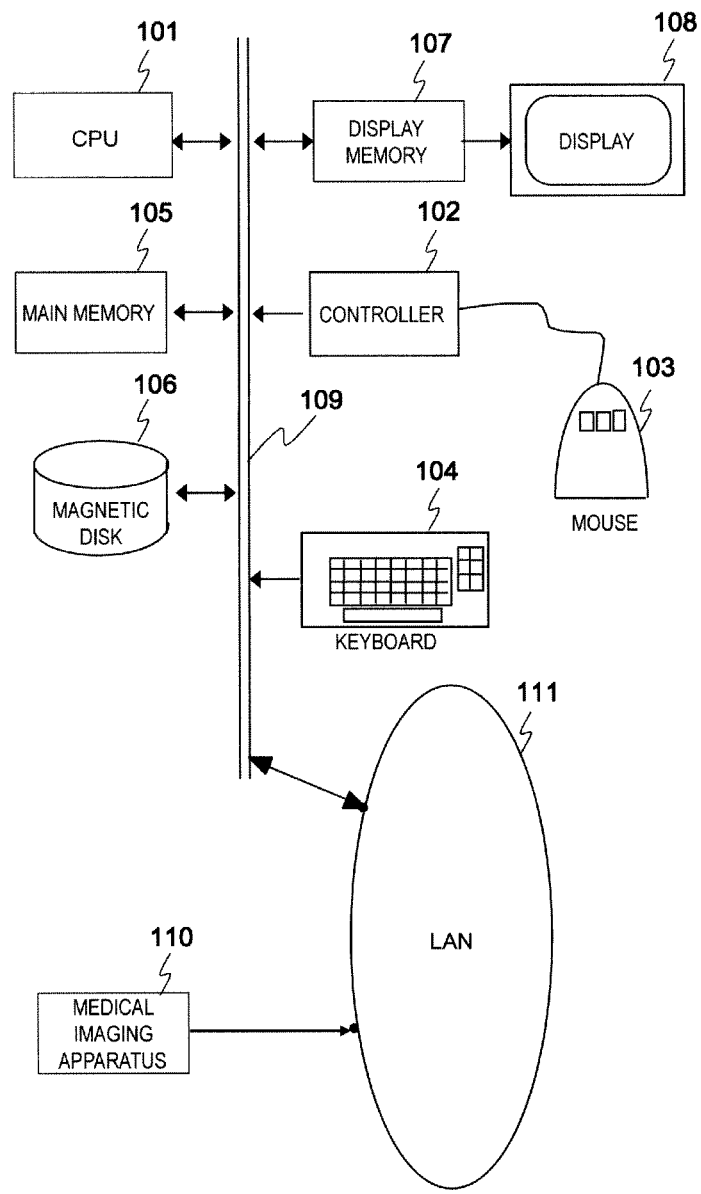

F I G . 3
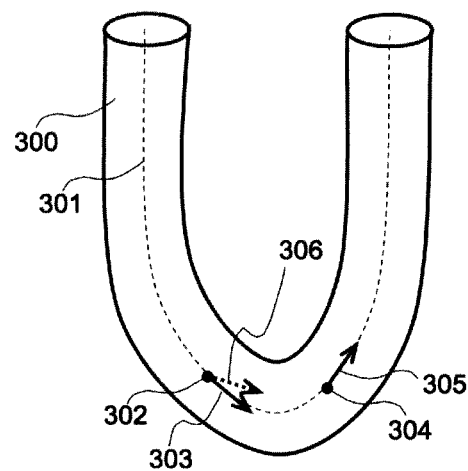

F I G . 4
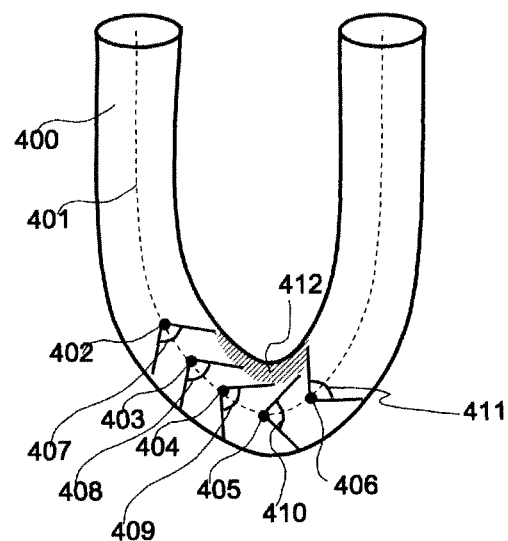
F I G . 5
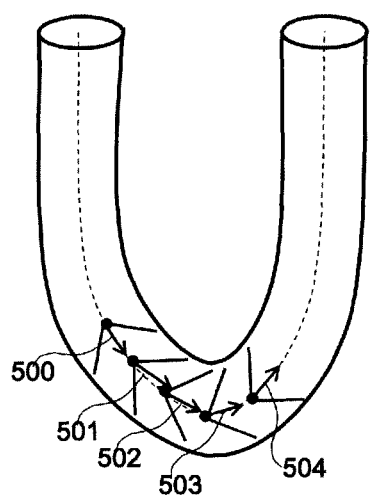

F I G . 8
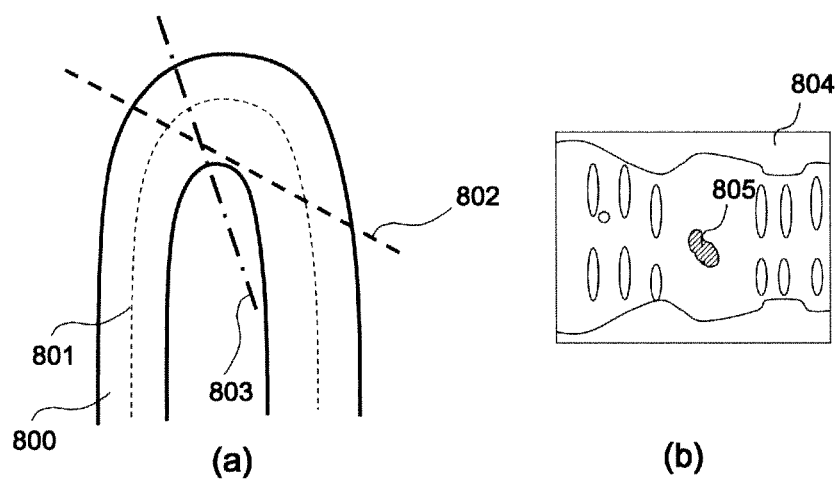
(a)   (b)
F I G . 9
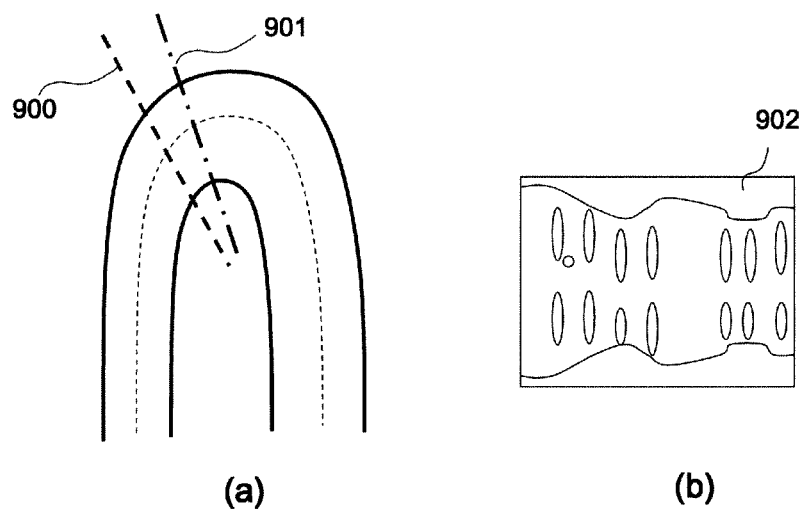
(a)   (b)

(a)　　　　　　　　　　　(b)

MEDICAL IMAGE DISPLAY DEVICE AND MEDICAL IMAGE DISPLAY METHOD

FIELD OF THE INVENTION

The present invention relates to a medical image display device and medical image display method, in particular to a medical image display device and medical image display method capable of providing medical images which are appropriate for diagnosis.

DESCRIPTION OF RELATED ART

In the conventional techniques, the following two image display methods have been used to diagnose inside of a hollow organ (for example, an intestines).

The conventional technique disclosed in Patent Document 1 displays the condition of organs such as intestines, bronchial tube and blood vessel as a virtual 3-dimensional image while moving an endoscopic viewpoint.

Also, the conventional technique disclosed in Patent Document 2 cuts through a hollow organ along the extended direction, performs panoramic projection on the wall surface of the hollow organ formed in approximately tubular shape, and 2-dimensionally displays it as a deployment image.

Patent Document 1: Japanese Patent No. 3632862
Patent Document 2: JP-A-H8-249492

However, the following problems still remains in the above-mentioned conventional techniques.

The hollow organs in an intestines, etc. have places that the extended direction thereof curves drastically. The conventional technique in Patent Document 1, in the respective viewpoints on the center line which passes through the center of the extended hollow organ (the line that connects the positions on which the viewpoints are sequentially placed in Patent Document 1), generates a pseudo-3-dimensional image in the tangent line direction of the center line. Therefore, when the hollow organ at the position placed slightly beyond the viewpoint curves drastically, the shadow of the drastically curved intestines generates a part that can not be displayed on a pseudo-3-dimensional image.

Also, in the conventional technique of Patent Document 2, in the respective set positions on the center line, a 2-dimensional image is generated based on the result of the projection performed on the plane which is orthogonal to the center line from the set position to the respective directions in the plane. However, in the places where the hollow organ drastically curves, there are cases that the planes which are orthogonal to the center line cross each other between the different respective set positions. In those cases, along with progress of the respective set positions in the hollow organ on the center line, the wall, etc. of the hollow organ often cannot be sequentially projected on the 2-dimensional plane and partly projected while being overlapped, which leads to generation of artifacts on a deployment image.

The objective of the present invention is to provide a medical image display device and medical image display method capable of generating high quality images even in the case that a hollow organ includes the places that curve drastically.

BRIEF SUMMARY OF THE INVENTION

In order to achieve the above-mentioned objective, the image display device of the present invention comprises:
storage means configured to store a slice image of an object to be examined which is obtained by a medical image diagnostic apparatus;
extraction means configured to extract the center line passing through the region and the center thereof of a hollow organ of the object from the slice image stored in the storage means; and
3-dimensional image generation means configured to generate a virtual 3-dimensional image of the inner wall of the hollow organ seen from a viewpoint while sequentially moving the viewpoint from one end to the other end of the center line,
and is characterized in further comprising means configured to change the direction in which the virtual 3-dimensional image seen from the viewpoint is generated to the direction of bending curvature of the hollow organ in accordance with the bending curvature thereof.

Also, the above-mentioned objective is achieved by the image display device comprising:
storage means configured to store a slice image of an object to be examined which is acquired by a medical image diagnostic apparatus;
extraction means configured to extract the center line passing through the region and the center thereof of the hollow organ from the slices image stored in the storage means; and
deployment image generation means configured to generate a deployment image of the hollow organ while moving a target point from one end to the other end of the center line, while executing the rendering process on the cross section which passes through the target point and is orthogonal to the center line,
characterized in further comprising means configured to change the direction in which the cross-section is to be set according to bending curvature of the hollow organ so as to prevent generation of artifacts in the deployment image.

Also, the above-mentioned objective is achieved by the image display device comprising:
(1) a step that stores a slice image of the object acquired by a medical image diagnostic apparatus;
(2) a step that extracts the center line passing through the region and the center thereof in the hollow organ of the object from the slice image stored in the storage means; and
(3) a 3-dimensional image generation step that generates a virtual 3-dimensional image of the inner wall of the hollow organ seen from a viewpoint while sequentially moving the viewpoint from one end to the other end of the center line, characterized in further comprising:
(4) a step that changes the direction in which the virtual e-dimensional image seen from the viewpoint is generated to the direction of bending curvature of the hollow organ according to the bending curvature thereof.

Also, the above-mentioned objective is achieved by the image display device comprising:
(1) a step that stores a slice image of the object which is acquired by a medical image diagnostic apparatus;
(2) step that extracts the center line passing through a region and the center thereof in the hollow organ of the object from the slice image stored in the storage means; and
(3) a step that generates a deployment image of the hollow organ while moving a target point from one end to the other end on the center line, passing through the target point and executing the rendering process on the cross-section which crosses the center line,
characterized in further comprising:
(4) a step that changes the direction in which the cross-section is to be set according to bending curvature of the hollow organ so as to prevent generation of artifacts.

In accordance with the present invention, it is possible to provide a medical image display device and medical image display method capable of generating high quality images even in the case that a hollow organ includes places that bend drastically.

BRIEF DESCRIPTION OF THE DIAGRAMS

Figure 2:
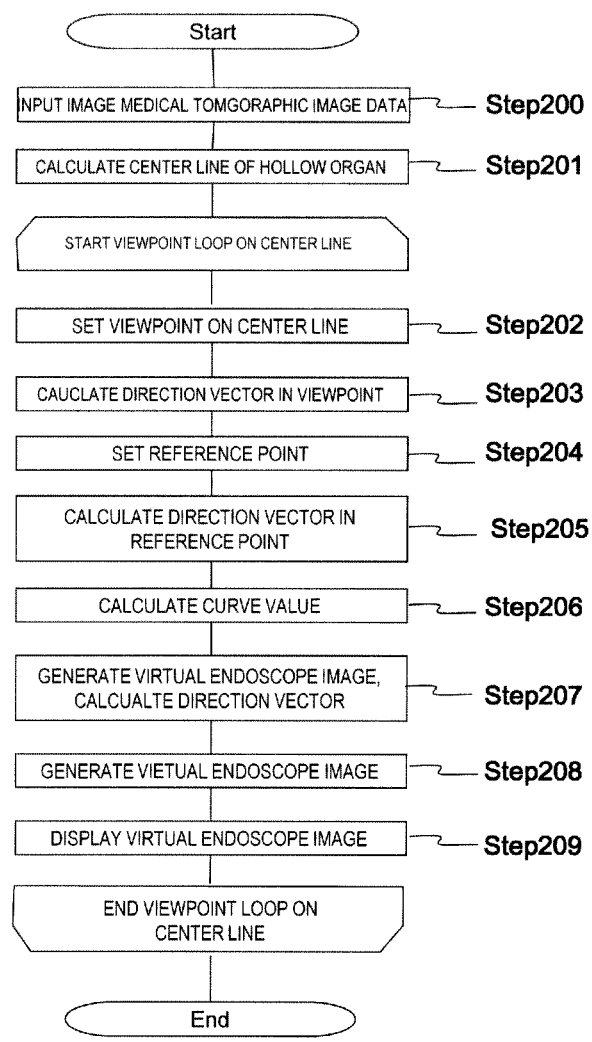
Figure 6:
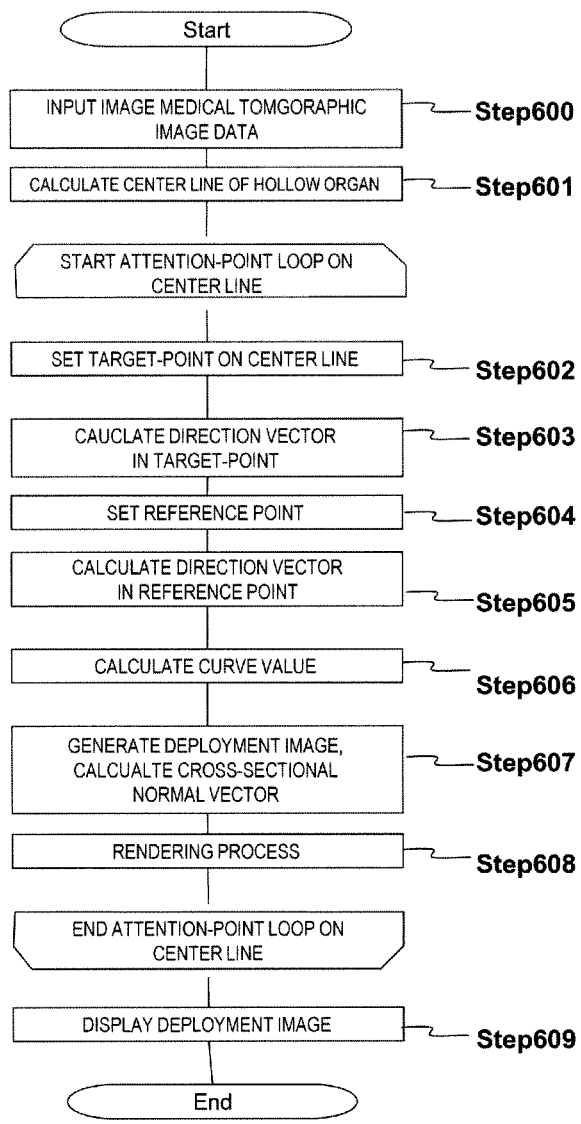
Figure 7:
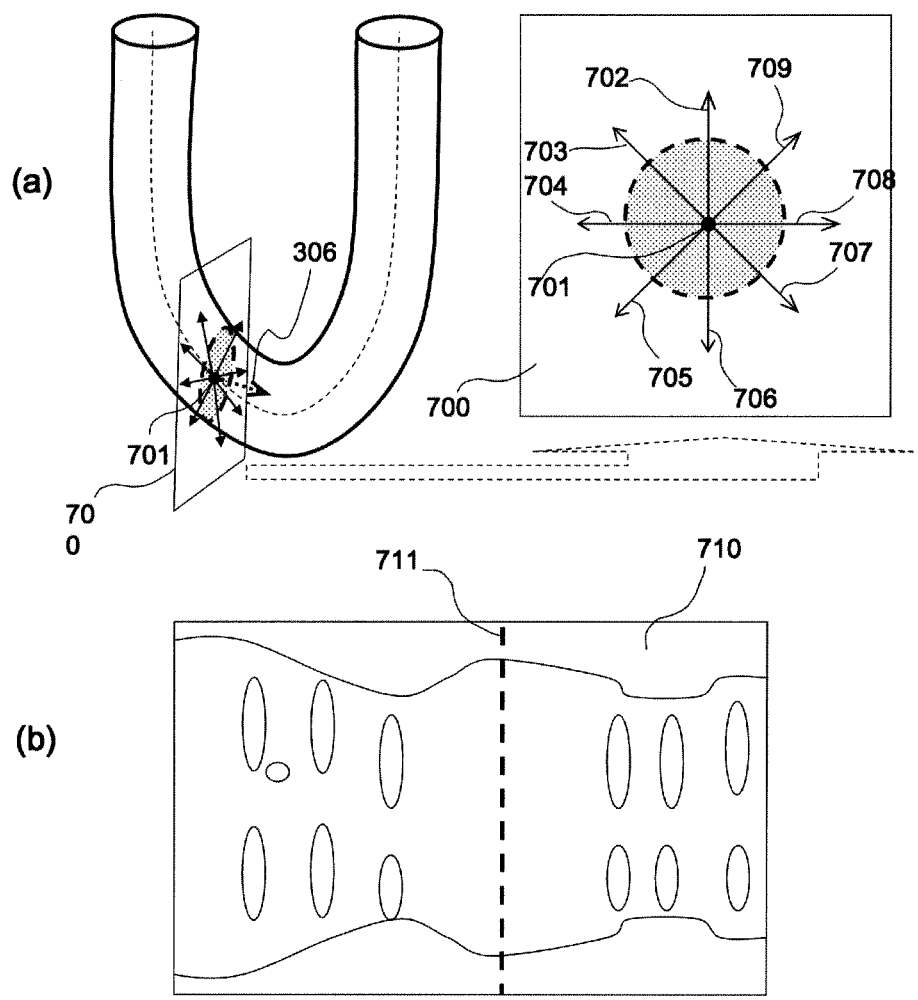
Figure 10:
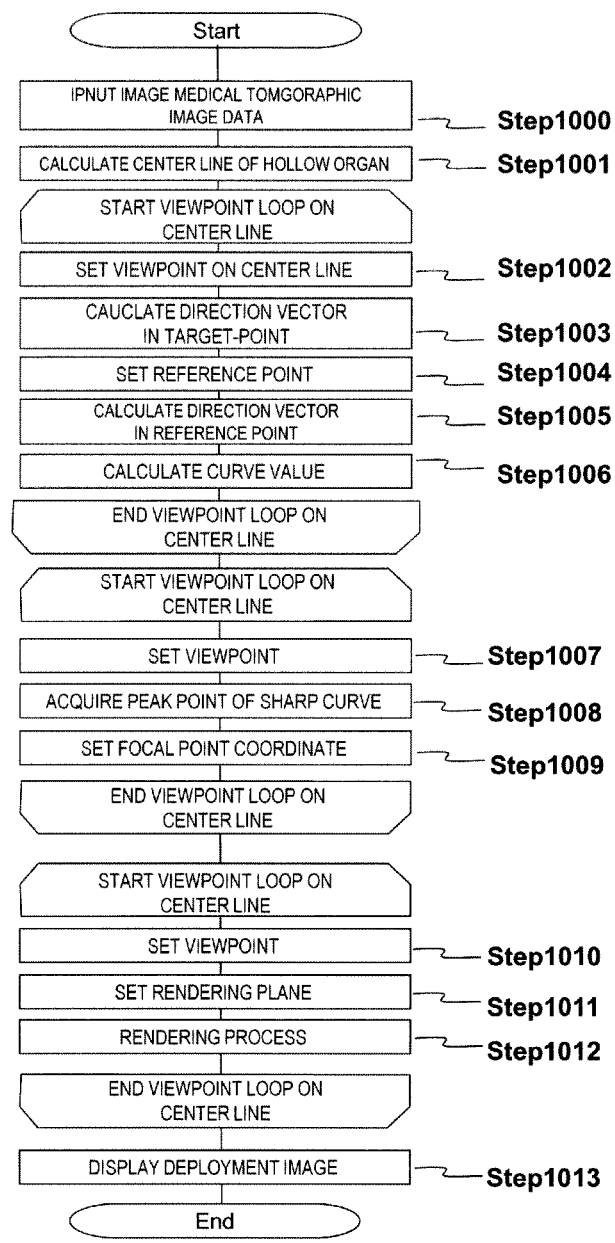
Figure 11:
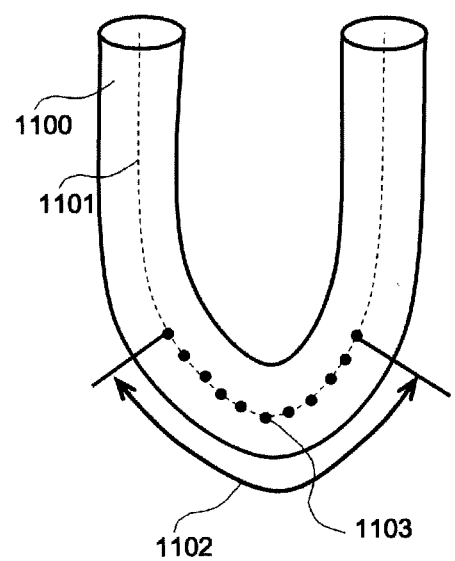
Figure 12:
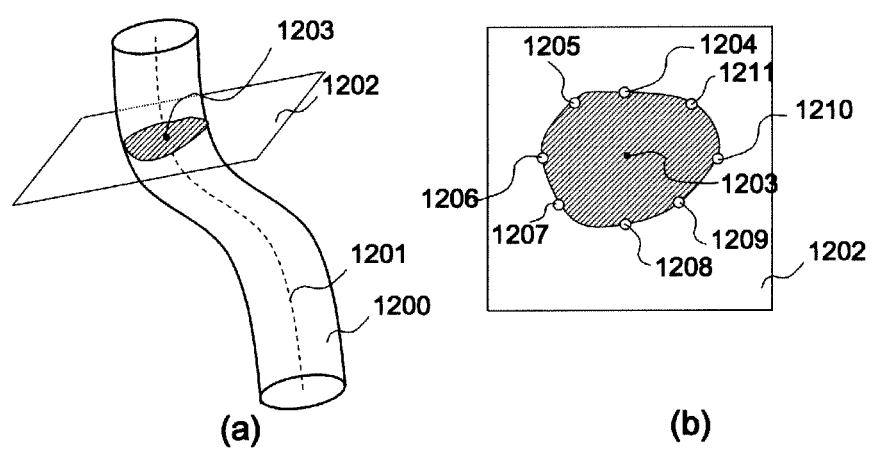
Figure 13:
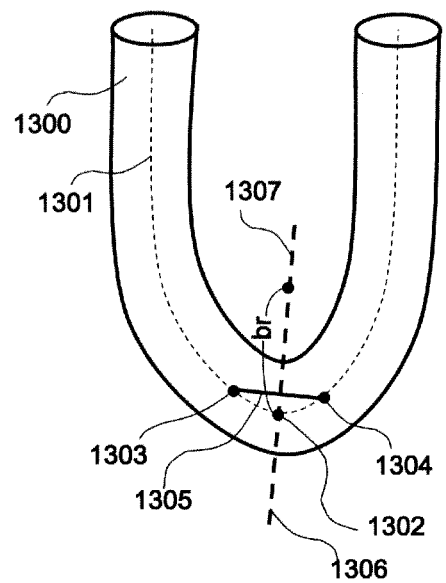
Figure 14:
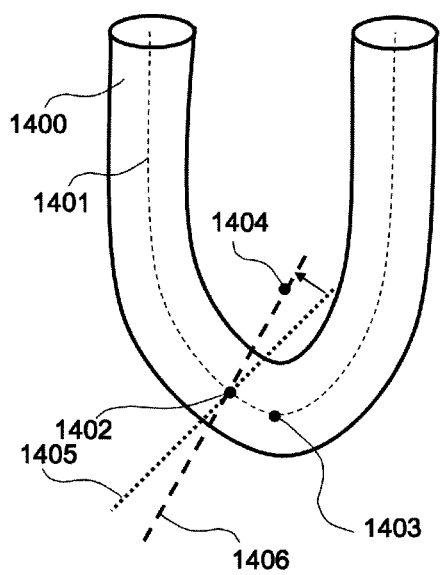
Figure 15:
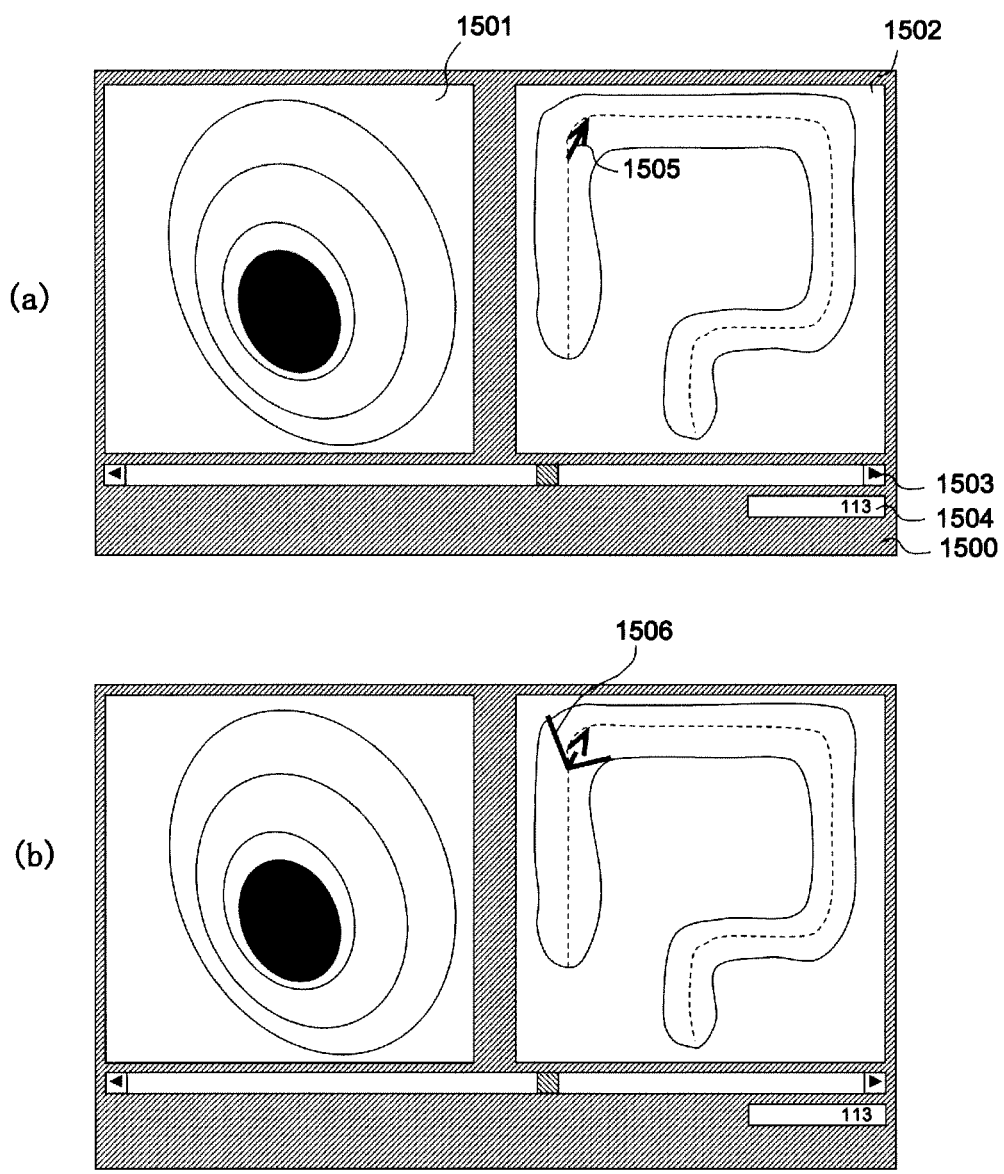
Figure 16:
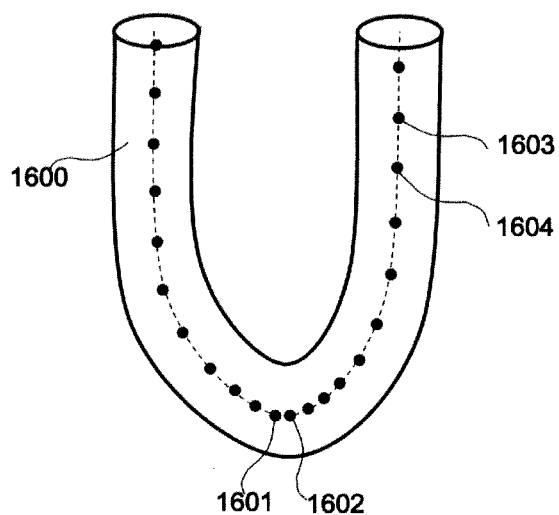
Figure 17:
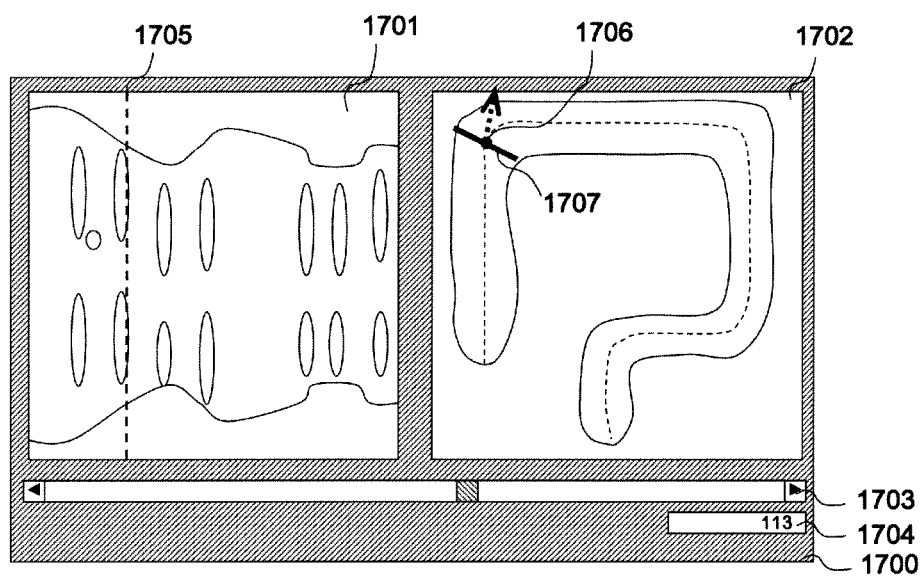

FIG. 1 is an example of a medical image display device related to the present invention.
FIG. 2 is a flowchart of embodiment 1 related to the present invention.
FIG. 3 is an explanatory diagram of embodiment 1 related to the present invention.
FIG. 4 illustrates a controversial point in a conventional method.
FIG. 5 shows effect of embodiment 1 related to the present invention.
FIG. 6 is a flowchart of embodiment 2 related to the present invention.
FIG. 7 is an explanation diagram of embodiment 2 related to the present invention.
FIG. 8 illustrates a controversial point in a conventional method.
FIG. 9 shows effect of embodiment 2 related to the present invention.
FIG. 10 shows a flowchart of embodiment 3 related to the present invention.
FIG. 11 is an explanatory diagram of embodiment 3 related to the present invention.
FIG. 12 is an explanatory diagram of embodiment 3 related to the present invention.
FIG. 13 is an explanatory diagram of embodiment 3 related to the present invention.
FIG. 14 is an explanatory diagram of embodiment 3 related to the present invention.
FIG. 15 is an explanatory diagram of embodiment 4 related to the present invention.
FIG. 16 is an explanatory diagram of embodiment 5 related to the present invention.
FIG. 17 is an explanatory diagram of embodiment 6 related to the present invention.

DESCRIPTION OF REFERENCE NUMERALS

101: CPU, 102: controller, 103: mouse, 104: keyboard, 105: main memory, 106: magnetic disk, 107: display memory, 108: display, 109: data transfer bus, 110: medical tomographic imaging apparatus, 111: LAN

DETAILED DESCRIPTION OF THE INVENTION

The embodiments of the present invention will be described below referring to the attached diagrams. In all diagrams for explaining the embodiments of the invention, the same function parts are represented by the same reference numerals, and the duplicative description thereof is omitted.

The CT image is used as a medical image and an intestinal canal is cited as a hollow organ which is an observation or diagnosis target in the following embodiments, the present invention is not limited to these embodiments. Any medical images taken by a medical image diagnostic apparatus capable of obtaining a tomographic image of an object such as an MRI apparatus, ultrasonic imaging apparatus, scintillation camera, PET device or SPECT device may be used as a medical image. Also, a hollow organ besides an intestinal canal such as a blood vessel or bronchial tube may be used as a target.

FIG. 1 shows an example of the image display device of the present invention. In the image display device, controller 102, keyboard 104, main memory 105, magnetic disk 106 and display memory 107 are respectively connected to CPU 101 via data transfer bus 109, while being capable of transmitting/receiving signals. CPU 101 is connected also to medical image diagnostic apparatus 110 via data transfer bus 109 and local area network (LAN) 111 while being capable of transmitting/receiving signals. Also, mouse 103 is connected to controller 102 and display 108 is connected to display memory 107 respectively while being capable of transmitting/receiving signals. Here, "being capable of transmitting/receiving signals" means that the signals can be reciprocally transmitted and received electrically and optically regardless of being wired or wireless.

CPU 101 executes computer programs, and controls the respective components that are connected to CPU 101. Concrete examples of the computer program are to acquire the center line passing through near the center of a hollow organ included in medical image data, to calculate the index indicating the degree of bending of the center line such as the curvature at the respective positions on the center line, or to create a virtual endoscope image of the hollow organ to be provided for diagnosis with small strain or a deployment image wherein the hollow organ is sliced open along the extended direction thereof according to the calculated index.

Controller 102 transmits various data such as displacement magnitude data of the position of mouse 103 which is detected by the sensor provided to the mouse or input data of a switch button provided in mouse 103 to CPU 101 via data transfer bus 109. An operator moves a cursor of mouse 103 to an image displayed on display 108 or a switch made by software such as a radio switch. The operator inputs predetermined input data by further clicking mouse 103 at the moved position. Keyboard 104 is an input device for inputting mainly letters such as ID information for specifying the medical image to be read out from magnetic disk 106 or a diagnostic report of the medical image displayed on display 108.

Main memory 105 is used as a working area of computer program such as for loading various computer programs from magnetic disk 106 or storing medical image data or intermediate steps of calculation upon calculation executed by various computer programs. Magnetic disk 106 receives computer program or a tomographic image of an object imaged by medical image diagnostic apparatus 110 via LAN 111 or data transfer bus 109, and stores the received information. Magnetic disk 106 here is a collective term of external storage devices in computer system. The external storage device includes all storage media such as a flexible disk, optical (magnetic) disk, ZIP memory and USB memory. Display memory 107 temporarily stores the data for displaying on a screen from among the calculation result executed by CPU 101 before transmitting signals to display 108.

Display 108 displays the medical images and variety of information thereof which are signal-transmitted from display memory 107.

Data transfer bus 109 transfers data between the respective components connected thereto according to the programs executed to CPU 101.

Medical image diagnostic apparatus 110 is for obtaining tomographic images such as an X-ray CT apparatus. LAN 111 capable of transmitting/receiving signals is used for connecting medical image diagnostic apparatus 110 and medical image display device. LAN may be a public circuit such as the internet.

Next, embodiments 1~6 will be described referring to the diagrams.

Embodiment 1

First embodiment of the present invention will be described using FIG. 1~FIG. 5. FIG. 2 shows the flowchart thereof. Embodiment 1 will be described according to the flowchart.

(Step 200)

An operator executes predetermined operations using an input device such as mouse 103 or keyboard 104, and inputs a medical tomographic image taken by medical image diagnostic apparatus 110, for example, a multi-slice image taken by an X-ray CT apparatus to main memory 105. In other words, the main memory is, in the present embodiment, used as storage means for storing the slice images of the object obtained by a medical image diagnostic apparatus.

(Step 201)

CPU 101 extracts the center line of a hollow organ to be the observation target using the hollow organ center line extraction method disclosed in, for example, JP-A-2006-42969 from the medical tomographic image inputted in step 200. More concretely, in paragraph number 0016 (step 63) of JP-A-2006-42969, the method is disclosed, in the region extraction method that extracts a whole blood vessel as moving a viewpoint forward while acquiring the cross-sectional regions which are orthogonal to the extended direction of the blood vessel considering continuity of the blood vessel region, to connect the line which passes the center of the blood vessel region by connecting the barycenters of the respective blood vessel cross-sectional regions acquired in the process of extraction. The present embodiment executes the method based on the above-described method. In this regard, while the center line which is acquired in the present embodiment is a curve, the curve thereof can be depicted by assembly of 3-dimensional positional coordinates formed by a row of multiple points, and the positional coordinate of the respective points are stored in a storage device. In other words, CPU 101 in the present step is used as extraction means to extract the center line passing through the region and the center thereof of the hollow organ of the object from the slice image stored by the storage means.

(Step 202)

CPU 101 sets a viewpoint for generating a virtual endoscope image, on the center line. In this embodiment, however, the viewpoint is set on the center line which is extracted in step 201 to display a virtual image by a moving image in such a way that as if an actual endoscope moves through inside of the hollow organ and gradually while renewing the viewpoint from one end to the other end of the center line. In other words, CPU 10 is to be used in the present embodiment as 3-dimensional image generation means for generating a virtual 3-dimensional image of the inner wall of the hollow organ viewed from the viewpoint being sequentially moved from one end to the other end of the center line as to be described in the steps below. Therefore, in step 202, one end of the center line which is extracted in step 201 is set first as the initial position of the viewpoint, the position of viewpoint is sequentially and gradually moved until it reaches the other end, and the process of step 203~209 are to be repeated as to be described below. Hereinafter, steps 203~209 which are to be executed while moving the viewpoint in step 202 will be described in order.

(Step 203)

CPU 101 calculates, at each viewpoint set in step 202, direction vector $D_E$ which makes the length 1, in the tangent line direction at the viewpoint. More concretely, CPU 101 calculates the direction vector of the line segment which connects each viewpoint and the adjacent viewpoint thereof from the assembly of the 3-dimensional positional coordinates used for depicting the center line, and adjusts the length of the vector to be unit length (1). In the present step, for example, as shown in FIG. 3, CPU 101 calculates direction vector 303 in the tangent line direction of center line 301 at viewpoint 302 on center line 302 in hollow organ 300 so as to make it as direction vector $D_E$ at the viewpoint.

(Step 204)

CPU 101 sets a reference point on the center line. Here, the reference point is to be used for calculating the degree of the curve in the vicinity of each viewpoint set in step 202. For example, the point which is moved forward from viewpoint 302 alongside of center line 301 for the portion of distance L is set as reference point 304. The value which is empirically obtained in advance may be constantly used for distance L, or an operator may arbitrarily set distance L using an input device such as mouse 103 or keyboard 104.

(Step 205)

CPU 101 calculates direction vector $D_R$ which makes its length 1 at the reference point set in step 204 using the same method as in step 203. For example, direction vector $D_R$ is to be calculated as direction vector 305 in the tangent line direction of the center line at reference point 304 as shown in FIG. 3.

(Step 206)

CPU 101 obtains index C indicating the degree of the curve (hereinafter referred to as "curve value") using direction vector $D_E$ at the viewpoint which is acquired in step 203 and direction vector $D_R$ at the reference point which is acquired in step 205. For example, index C sets inner product of the two vectors as the curve value as shown in expression 1.

$$C = \vec{D_E} \cdot \vec{D_R} \quad \text{(expression 1)}$$

When the inner product as shown in the expression (1) is selected as index C, if the value is greater the curve becomes moderate and if the value is smaller the curve becomes sharper.

(Step 207)

CPU 101 obtains direction vector $D_V$ for creating a virtual endoscope image using the curve value C which is acquired in step 206. For example, direction vector $D_V$ is set according to expression (2).

$$\vec{D_V} = \vec{D_E} + \alpha(1.0 - C)\vec{D_R} \quad \text{(expression 2)}$$

Here, the coefficient which is empirically determined may be used for proportionality constant "a", or an operator may arbitrarily set the coefficient for proportionality constant "a" using an input device such as mouse 103 or keyboard 104. For example, direction vector $D_V$ in which the virtual endoscope image is created is to be calculated as direction vector 306 as shown in FIG. 3. When the direction vector for creating the virtual endoscope image is selected as shown in the expression (2), since the direction vector which was originally $D_E$ direction changes the direction in the second term of the right-hand side of expression (2), the direction in which the virtual endoscope image is created is tilted to the direction that the hollow organ curves.

(Step 208)

CPU 101 creates a virtual endoscope image in direction $D_V$ which is acquired in step 207 using the method for creating the virtual endoscope image disclosed, for example, in Patent Document 1. Therefore in the present embodiment, according to the curve of the hollow organ, CPU 101 is used as means to change the direction in which the virtual 3-dimensional image viewed from the viewpoint, to the direction of the curve.

Here, value which is empirically determined may be used for the view range for creating the virtual endoscope image (hereinafter referred to as "view angle"), or an operator may arbitrarily set the view angle using an input device such as mouse 103 or keyboard 104.

(Step 209)

CPU 101 displays the virtual endoscope image created in step 208 on display 108.

As described above, the medical image display device and the medical image display method in the present embodiment is effective in improving accuracy in examining the inner wall area of a hollow organ of an object, since even the portion in the viewpoint that is shaded due to the region which curves drastically in a virtual endoscope image can be seen by the fine adjustment of the direction vectors for creating the virtual endoscope image. As a result, it is possible to reduce the possibility of missing diseased areas in observation of a diagnostic image.

For example, FIG. 4 illustrates the conventional case that the direction orthogonal to centerline 401 in hollow organ 400 is made as the direction for creating the virtual endoscope image. Here, the virtual endoscope images of viewpoint angles 407~411 are created at viewpoints 402~406, and observation is carried out while the images are transmitted sequentially. However, region 412 becomes the blind area and cannot be observed. On the other hand, FIG. 5 illustrates the case that the virtual endoscope images are acquired in creation directions 500~504 using the present embodiment. Here, the method for creating virtual endoscope images of the region where a hollow organ is curved drastically is illustrated, and there is no portion being the shadow of the viewpoint which has been a problem in the conventional technique.

While the curve value is defined here as expression 1, different values such as curvature may be used for the curve value. It is preferable to use the index wherein calculation can be quickly executed as in expression 1.

Also, for parameter L or proportionality constant "a" for calculating the curve value, the value of a function having the viewpoint angle of the virtual endoscope as variable may be set instead of using the values which are empirically acquired or arbitrarily set by an operator. For example, when the view angle is large, it is preferable to set a small value of distant L or proportionality constant "a" since the influence due to drastic change in the extending direction of the hollow organ is not very great. Also, when the view angle is small, it is preferable to set a large value of distant L or proportionality constant "a" large since the influence due to drastic change in the extending direction of the hollow organ is great.

Also, in the present embodiment, since the direction in which a virtual 3-dimensional image is created is changed according to the expression (2), means to change the direction for creating the virtual 3-dimensional image viewed from the viewpoint to the direction of the bending curvature is capable of changing the direction for creating the virtual 3-dimensional image viewed from the viewpoint more greatly when the degree of bending curvature is greater. In the present embodiment, degree of the bending curvature is expressed in the expression (1), by the inner product of the unit vector in the tangent line direction at each viewpoint position and the unit vector in the tangent line direction at the position which is apart from each specified position for a predetermined distance.

Embodiment 2

Embodiment 2 in the present invention will be described referring to FIG. 1, FIG. 3, FIG. 6 and FIG. 7. The flowchart of embodiment 2 will be shown in FIG. 6, and Embodiment 2 will be described according to this flowchart. In embodiment 2, the example of the case for creating a deployment image wherein a hollow organ is cut open in its extended direction will be cited.

Step 600~step 607 will be omitted here since they are practically the same as step 200~step 207 in embodiment 1. In the present embodiment, a viewpoint is replaced by a target point, and a virtual endoscope image is replaced by a deployment image.

(Step 608)

CPU 101 executes the rendering process, as shown in FIG. 7, by radially positioning line segments referred to as rays (702~709) from target point 701 by predetermined angles (for example by 45-degrees) in cross section 700 (FIG. 7(*a*)) having normal vector 306 which is acquired in step 607. The result of the rendering process is to be reflected in line 711 on deployment image 710 (FIG. 7(*b*)).

(Step 609)

CPU 101 displays the deployment image which is obtained by repeating the process of steps 602~608 at the respective target points on the center line, on display 108.

CPU 101 is used as means to create a deployment image of the hollow organ, while moving a target point from one end to the other end of the center line, by executing the rendering process on the cross section which passes through the target point and is orthogonal to the center line, and is also used as means to change the direction for setting the cross section according to the bending curvature of the hollow organ so as to prevent generation of artifacts.

In this embodiment, since the direction in which a deployment image is created is changed according to the expression (2) shown in embodiment 1, means to change the direction for creating the deployment image viewed from the target point to the direction of the bending curvature is capable of changing the direction for creating the deployment image viewed from the target point more greatly when the degree of bending curvature is greater. In the present embodiment, degree of the bending curvature is expressed in the expression (1), by the inner product of the unit vector in the tangent line at each viewpoint position and the unit vector in the tangent line at the position which is apart from each specified position for a predetermined distance. Also, degree of the bending curvature may be expressed by the measure of the curvature at the respective target points.

As described above, the medical image display device and medical image display method of the present embodiment is effective in improving accuracy in examining an inner wall area of a hollow organ of an object where the hollow organ drastically curves. The specific effect of the present embodiment is that deployment images, more specifically the inner wall, etc. of a hollow organ with less strain even in sharp curves is sequentially projected on a 2-dimensional plane, and is possible to provide deployment images without partially overlapped projection thus without artifacts.

FIG. 8 and FIG. 9 show concrete examples of effect of the present embodiment. FIG. 8 shows a sharp curve region, and when the cross-section for creating a deployment image of hollow organ 800 in the direction orthogonal to center line

801 is set as in the past in the respective target points in the conventional manner, there are places that the cross-sections cross each other between the target points that are close to each other (such as plane 802 and plane 803) (FIG. 8(*a*)). This crossing of cross sections (hereinafter referred also to as ray cast planes) often causes artifact 805 on deployment image 804 (FIG. 8(*b*)).

On the other hand, by using the present embodiment as shown in FIG. 9, the cross sections for creating deployment images (ray cast planes) such as plane 900 and plane 901 (FIG. 9(*a*)) do not cross each other even in a sharp curve, whereby making it possible to provide deployment image 902 with less strain (FIG. 9(*b*)).

Embodiment 3

Embodiment 3 of the present embodiment will be described referring to FIG. 1 and FIG. 10~FIG. 14. FIG. 10 shows a flowchart of embodiment 3. Embodiment 3 will be described according to this flowchart. In embodiment 3, the example of the case for creating a deployment image wherein a hollow organ is cut open in its extended direction will be cited.

(Step 1000)
An operator executes a predetermined operation using an input device such as mouse 103 or keyboard 104, and inputs the medical tomographic image which is taken by medical image diagnostic apparatus 110 (for example, a multi-slice image) to main memory 105.

(Step 1001)
CPU 101 extracts the center line of the target hollow organ from the medical tomographic image inputted in step 1000 using the center-line extracting method of hollow organs disclosed in, for example, JP-A-2006-42969 as described in embodiment 1.

(Step 1002)
CPU 101 sets the target point for calculating the index which indicates the degree of a curve in the hollow organ (hereinafter referred to as "curve value") on the center line. More concretely, in the present embodiment, by moving the position of the target point in small steps from the start point to the end point of the center line extracted in step 1001, and repeats the curve value calculation process indicated below in steps 1003~1006.

(Step 103)
CPU 101 calculates direction vector $D_E$ which makes the measure 1 in the tangent direction of the target point at each target point set in step 1002 using the method described in step 203 of embodiment 1.

(Step 104)
CPU 101 sets a reference point on the center line using the method described in step 204 of embodiment 1 (step 1005).

CPU 101 calculates direction vector $D_R$ which makes the length 1 at the reference point set in step 1004 using the same method as step 203.

(Step 1006)
CPU 101 obtains index C which indicates the degree of a curve (hereinafter referred to as a "curve value") using direction vector $D_E$ of the target point acquired in step 1003 and direction vector $D_R$ of the reference point acquired in step 1005, using the method described in step 206 of embodiment 1. For example, as shown in expression (3), the inner product of the two vectors is set as the curve value in index C.

$$C = \vec{D_E} \cdot \vec{D_R}$$ (expression 3)

(Step 1007)
CPU 101 acquires the focal point to be used for creating a deployment image in steps 1007~1009. For that purpose, range of the target point for setting the focal point to be used for creating the deployment image is set on the center line. The range of the target point is to be set, out of all the points from the start point to the endpoint on the center line extracted in step 1001, at the point wherein the curve value acquired in step 1006 is less or equal than a predetermined value. While the threshold value need to be set so that a sharp curve region falls within the value equal or less than the predetermined value, the threshold value maybe the empirically determined value or the value set by an operator as desired using an input device such as mouse 103 or keyboard 104.

(Step 1008)
CPU 101 obtains the point to be at the peak of the curve out of the continuing points, from among the target points which belong to the sharp curve region set in step 1007. The apex of the curve can be obtained, for example, by acquiring the displacement of the coordinate which forms the center line by second order differential, and using the inflexion point thereof. For example, as shown in FIG. 11, the apex of the curve can be obtained as point 1103 with respect to sharp curve region 1102 on center line 1101 which is extracted in hollow organ 1100.

(Step 1009)
CPU 101 obtains the focal point to be used for creating a deployment image using the apex coordinate of the curve acquired in step 1008. The method for acquiring the focal point will be described using FIG. 12 and FIG. 13. Radius r of a hollow organ at the apex of the curve is obtained. Radius r of the hollow organ may be, for example, the average value of the distance from point 1203 on the center line to a plurality of points 1204~1211 on the intraluminal wall in cross section 1202 which is orthogonal to center line 1201 of hollow organ 1200 shown in FIG. 12 (FIG. 12(*a*)(*b*)). Or, by performing circle approximation on points 1204~1211 on the intraluminal wall and the radius thereof may be set as radius r. While 8 points on the intraluminal wall are used here for the sake of explanation, the number of points can be more or less than 8. After obtaining the radius, as shown in FIG. 13, straight line 1306 which passes through apex 1302 of the target curve on center line 1301 of hallow organ 1300 and is orthogonal to line segment 1305 which connects two points that are in ahead and behind of apex 1302 (points 1303 and 1304). Point 1307 which is apart from apex 1302 on straight line 1306 for the portion of distance br is set as the focal point. Here, b is a coefficient, and it may be the empirically acquired value or may be arbitrarily set by an operator using an input device such as mouse 103 or keyboard 104. The point acquired here is applied to all of the points which belong to the same sharp curve region.

(Step 1010)
CPU 101 sets a target point for creating a deployment image. Here, the viewpoint belongs to the portion from the start point to the end point of the range for creating the deployment image out of the center line which is extracted in step 1001, and steps 1010~1012 are to be repeated while renewing the viewpoint.

(Step 1011)
CPU 101 sets the plane for executing the rendering including the target point for the creation of the deployment image. In this setting, the setting method is changed depending on whether the target point belongs to the sharp curve region acquired in step 1008 or not. When the viewpoint does not belong to the sharp curve region, the cross section which passes through the viewpoint and is orthogonal to the center line is set as the rendering plane. On the other hand, the rendering plane setting method in the case that the viewpoint belongs to the sharp curve region will be described using FIG. 14. Here, the case is considered that the rendering plane corresponding to target point 1402 on center line 1401 of hollow organ 1400 is to be set. The apex of the sharp curve acquired in step 1008 and the focal point acquired in step 1009 are set here as point 1403 and point 1404 respectively. Also, plane 1405 is assumed to pass through target point 1402 and is orthogonal to center line 1401. In the case that the viewpoint belongs to the sharp curve region, plane 1406 wherein plane 1405 is rotated so as to include point 1404 is set as the rendering plane.

(Step 1012)

CPU 101 executes the rendering process by radially setting the line segments which is referred to as the ray from the target point on the center line toward intraluminal wall with respect to the plane set in step 1011. The rendering result in the respective rays is set as the pixel value of the corresponding pixels on the deployment image.

(Step 1013)

CPU 101 displays the deployment image created by the processes up to step 1012 on display 108.

As described above, the medical image display device and medical image display method of the present embodiment is effective in improving accuracy in examining the inner wall area in the observing organ of an object in the region where the hollow organ drastically curves. Also, the specific effect of the present embodiment is to provide deployment images with less strain even in sharp curve regions, which leads to improvement of diagnostic efficiency.

While the curve value is defined as seen in expression 3 here, other values such as curvature may be used as the curve value. In this regard, however, that it is desirable that the index can be calculated quickly as in expression 3.

Embodiment 4

Embodiment 4 of the present invention will be described below using FIG. 15.

In embodiment 1, the method for reducing dead spaces upon creating virtual endoscope images is exemplified. In embodiment 4, the case will be exemplified that the created virtual endoscope image and the direction of the central viewpoint thereof are displayed on graphical user interface (hereinafter referred to as GUI).

CPU 101 displays the virtual endoscope image at the respective viewpoints created by the processing flow shown in FIG. 2, on GUI 1500 displayed on display 108 (for example, virtual endoscope image 1501). At the same time, 3-dimensional image 1502 of the target hollow organ is displayed on GUI 1500. The operator operates viewpoint number setting scroll bar 1503 or viewpoint number setting edit 1504 on GUI 1500 using an input device such as mouse 103 or keyboard 104, and sets the desired viewpoint number for displaying the virtual endoscope image (FIG. 15(*a*)).

On 3-dimensional image 1502, the viewpoint direction of the virtual endoscope image is displayed as arrow 1505 at the position corresponding to the display viewpoint number. In this manner, the medical image display device and medical image display method of the present embodiment is effective in improving efficiency and accuracy in examining the inner wall area of a hollow organ in an object in the region where the hollow organ drastically curves. Also, the specific effect of the present embodiment is that the position and the direction in which a virtual endoscope image viewed at the present time can be recognized at a glance.

As shown in FIG. 15(*b*), viewpoint range 1506 may be displayed besides viewpoint direction 1505.

Embodiment 5

Embodiment 5 of the present invention will be described below referring to FIG. 16. In embodiment 1, the intervals of the viewpoints at which a virtual endoscope image is created are described assuming that they are equally spaced. In FIG. 5, the case that the intervals of the viewpoints are varied according to constant rule will be described. Using curve value C acquired in expression 1 of embodiment 1, distance d from the current viewpoint to the next viewpoint is set, for example, as shown in expression 4.

$$d = k(C+1) \qquad (4)$$

Here, value which is empirically obtained may be used for k, or an operator may arbitrarily set k using an input device such as mouse 103 or keyboard 104. For example, on hollow organ 1600, the interval between viewpoints in the region of the hollow organ having a sharp curve become narrow as seen in viewpoint 1601 and viewpoint 1602, and the interval between viewpoints in the region having a moderate curve become wide as seen in viewpoint 1603 and viewpoint 1604.

In other words, in the present embodiment, the intervals between viewpoints to be sequentially moved are varied in accordance with bending curvature of the hollow organ.

In this manner, the medical image display device and medical image display method of the present embodiment is effective in improving efficiency and accuracy in examining the inner wall area of a hollow organ of an object in the region where the hollow organ drastically curves. Also, the specific effect of the present embodiment is, in the case that the operator performs observation while renewing the viewpoint such as creating virtual endoscope images, that accuracy in observing the curve region where it is easy to miss the information can be improved since the intervals of viewpoints are narrower in sharper curves. Also, the present embodiment can be applied also to interval setting of target points in the case of sequentially creating deployment images described in embodiment 2.

Embodiment 6

Embodiment 6 of the present invention will be described below referring to FIG. 17.

In embodiment 2 and embodiment 3, the method for creating a deployment image of a hollow organ while reducing strain is exemplified. In embodiment 6, the case that the relationship between the position on the created deployment image and the position on the 3-dimensional image thereof is displayed on graphical user interface (hereinafter referred to as GUI) will be exemplified.

CPU 101 displays the deployment image created by the processing flow shown in FIG. 6 or FIG. 10 on GUI 1700 which is displayed on display 108 (for example, deployment image 1701). At the same time, 3-dimensional image 1702 of the hollow organ as an observation target is to be displayed on GUI 1700. When the operator operates viewpoint number setting scroll bar 1703 or target point number setting edit 1704 on GUI 1700 using an input device such as mouse 103 or keyboard 104, line 1705 indicating the position of the target point which is displayed on the deployment image moves. Or, it may be set so that line 1705 can be directly moved by the operator using mouse-dragging. When line 1705 is moved, viewpoint 1706 and cross-sectional position 1707 is simultaneously displayed at the corresponding positions on 3-dimensional image 1702. In this manner, the medical image display device and medical image display method of the present embodiment is effective in improving efficiency and accuracy in examining the inner wall area of a hollow organ of an object in the region where the hollow organ drastically curves. In this manner, the medical image display device and medical image display method of the present embodiment is effective in improving efficiency and accuracy in examining the inner wall area of a hollow organ of an object in the region where the hollow organ drastically curves. Also, the specific effect of the present embodiment is that the presently indicating position on a deployment image and the position thereof on a 3-dimensional image can be corresponded in one glance.

The preferable embodiments of the medical image display device and medical image display method according to the present invention have been described above. However, the present invention is not limited to these embodiments. It is obvious that persons skilled in the art can make various kinds of alterations or modifications within the scope of the technical idea disclosed in this application, and it is understandable that they belong to the technical scope of the present invention.

DIAGRAMS

FIG. 1
102 CONTROLLER
103 MOUSE
104 KEYBOARD
105 MAIN MEMORY
106 MAGNETIC DISK
107 DISPLAY MEMORY
108 DISPLAY
110 MEDICAL IMAGE DIAGNOSTIC APPARATUS
FIG. 2
Step 200 INPUT IMAGE MEDICAL TOMOGRAPHIC IMAGE DATA
Step 201 CALCULATE CENTER LINE OF HOLLOW ORGAN START VIEWPOINT LOOP ON CENTER LINE
Step 202 SET VIEWPOINT ON CENTER LINE
Step 203 CALCULATE DIRECTION VECTOR AT VIEWPOINT
Step 204 SET REFERENCE POINT
Step 205 CALCULATE DIRECTION VECTOR AT REFERENCE POINT
Step 206 CALCULATE CURVE VALUE
Step 207 GENERATE VIRTUAL ENDOSCOPE IMAGE, CALCULATE DIRECTION VECTOR
Step 208 GENERATE VIRTUAL ENDOSCOPE IMAGE
Step 209 DISPLAY VIRTUAL ENDOSCOPE IMAGE END VIEWPOINT LOOP ON CENTER LINE
FIG. 6
Step 600 INPUT IMAGE MEDICAL TOMGORAPHIC IMAGE DATA
Step 601 CALCULATE CENTER LINE OF HOLLOW ORGAN START TARGET-POINT LOOP ON CENTER LINE
Step 602 SET TARGET-POINT ON CENTER LINE
Step 603 CALCULATE DIRECTION VECTOR AT TARGET-POINT
Step 604 SET REFERENCE POINT
Step 605 CALCULATE DIRECTION VECTOR AT REFERENCE POINT
Step 606 CALCULATE CURVE VALUE
Step 607 GENERATE DEPLOYMENT IMAGE, CALCULATE CROSS-SECTIONAL NORMAL VECTOR
Step 608 RENDERING PROCESS END ATTENTION-POINT LOOP ON CENTER LINE
Step 609 DISPLAY DEPLOYMENT IMAGE
FIG. 10
Step 1000 INPUT IMAGE MEDICAL TOMOGRAPHIC IMAGE DATA
Step 1001 CALCULATE CENTER LINE OF HOLLOW ORGAN START VIEWPOINT LOOP ON CENTER LINE
Step 1002 SET VIEWPOINT ON CENTER LINE
Step 1003 CALCULATE DIRECTION VECTOR AT A TARGET-POINT
Step 1004 SET REFERENCE POINT
Step 1005 CALCULATE DIRECTION VECTOR AT REFERENCE POINT
Step 1006 CALCULATE CURVE VALUE END VIEWPOINT LOOP ON CENTER LINE START VIEWPOINT LOOP ON CENTER LINE
Step 1007 SET VIEWPOINT
Step 1008 ACQUIRE PEAK POINT OF SHARP CURVE
Step 1009 SET FOCAL POINT COORDINATE
Step 1010 SET VIEWPOINT
Step 1011 SET RENDERING PLANE
Step 1012 RENDERING PROCESS END VIEWPOINT LOOP ON CENTER LINE DISPLAY DEPLOYMENT IMAGE END

The invention claimed is:

1. A medical image display device comprising:
storage means configured to store a slice image of an object to be examined which is obtained by a medical image diagnostic apparatus;
extraction means configured to extract a center line passing through a region of a hollow organ of the object and a center thereof from the slice image stored in the storage means;
deployment image generation means configured to generate a deployment image of the hollow organ while moving a target point from one end to the other end on the center line and executing a rendering process on a cross-section which passes through the target point and is orthogonal to the center line; and
setting means configured to set a direction of the cross-section including a focal point which is set using an apex of bending curvature of the hollow organ so as to prevent generation of artifacts,
wherein the setting means sets the focal point on a straight line which passes through the apex and is orthogonal to a line segment which connects two points that are disposed ahead and behind, respectively, of the apex.

2. The medical image display device according to claim 1, wherein the setting means sets the focal point at a distance, which is set by multiplying a coefficient and a radius of the hollow organ at the apex, from the apex on the straight line.

3. The medical image display device according to claim 1, wherein the setting means sets the focal point by using points on the center line in a range in which a degree of the bending curvature is less than or equal than a predetermined value.

4. A medical image display method comprising:
a storing step that stores a slice image of an object to be examined which is acquired by a medical image diagnostic apparatus;
a step that extracts a region of a hollow organ in the object and a center line which passes through a center thereof from the slice image stored by the storing step;

a step that generates a deployment image of the hollow organ while moving a target point from one end to the other end on the center line and executing a rendering process on a cross section which passes through the target point and is orthogonal to the center line; and setting a direction of the cross-section including a focal point which is set using an apex of bending curvature of the hollow organ so as to prevent generation of artifacts, setting the focal point on a straight line which passes through the apex and is orthogonal to a line segment which connects two points that are disposed ahead and behind, respectively, of the apex.

\* \* \* \* \*